United States Patent [19]
Hanna

[11] 3,946,729
[45] Mar. 30, 1976

[54] VENTILATOR PATIENT MONITOR

[75] Inventor: Kim L. Hanna, Acton, Mass.

[73] Assignee: Hewlett-Packard Company, Palo Alto, Calif.

[22] Filed: Oct. 17, 1974

[21] Appl. No.: 515,801

[52] U.S. Cl. ...... 128/145.8; 128/DIG. 29; 128/2.08; 73/194 R
[51] Int. Cl.² .................................... A61M 16/00
[58] Field of Search ......... 128/145.5–145.8, 142–142.3, 203, 188, DIG. 17, 2.08, 2.07, DIG. 29; 73/194 R, 194 E, 194 M, 195 R

[56] References Cited
UNITED STATES PATENTS

| | | | |
|---|---|---|---|
| 3,033,195 | 5/1962 | Gilroy et al. | 128/145.8 |
| 3,759,249 | 9/1973 | Fletcher | 73/194 M |
| 3,768,468 | 10/1973 | Cox | 128/145.8 |
| 3,894,536 | 7/1975 | Tysk | 128/145.8 |

Primary Examiner—Ronald L. Frinks
Assistant Examiner—Henry J. Recla
Attorney, Agent, or Firm—Stephen P. Fox; Allston L. Jones

[57] ABSTRACT

A method and apparatus for obtaining an accurate measure of the gas volume expired by a patient by deriving a signal that provides a positive indication of when the patient is exhaling. This signal is used to limit the gas flow monitoring to the expired flow of the patient, thus eliminating the monitoring of a gas volume that leaks through a partially closed ventilator expiration valve during patient inspiration. The gas flow through the expiration valve and the mouth pressure of the patient are used to obtain an indication of the resistance of the expiration valve. This resistance indication is then compared with a preselected threshold valve resistance to accurately determine the time of expiration.

13 Claims, 5 Drawing Figures

VENTILATOR PATIENT MONITOR

BACKGROUND OF THE INVENTION

This invention is concerned generally with medical electronics, and, more particularly, with ventilator patient monitors.

A ventilator is used to provide supplemental or complete respiration for a patient when the patient is unable to maintain sufficient respiration without assistance. The majority of ventilators used for supplemental or complete patient respiration are of the type known as intermittent positive pressure breathing (IPPB) ventilators. An IPPB ventilator provides positive pressure to force air into the lungs of the patient to accomplish inspiration. Inspiration is then followed by expiration by the patient without assistance. This cycle is then repeated at a predetermined rate.

The typical IPPB ventilator system comprises a gas supply, a pumping mechanism, interconnection tubing to the patient, an expiration valve with an input port and an output port, and either an electrical or a pneumatic control line from the pumping mechanism to the expiration valve. The tubing includes a tee connector and three lengths of tubing. One tube is connected between the pumping mechanism and one of the two coaxial stems of the tee connector, a second tube is connected between the input port of the expiration valve and the second of the coaxial stems of the tee connector, and a third tube is connected between the third stem of the tee connector and the patient.

The expiration valve is a low pressure pneumatic valve which typically experiences a maximum internal gas flow pressure of 0.9 to 1.2 PSI. Control of gas flow through the valve is performed by an electrically or pneumatically activated diaphragm in the flow stream to open and close the valve. The majority of the IPPB ventilators utilize a pneumatic valve control signal. In the pneumatically controlled expiration valve, the diaphragm is analogous to a small balloon in a pipe which is inflated by the pneumatic signal from the ventilator pumping mechanism to provide valve closure. The diaphragm deflates when the pneumatic signal is relaxed, allowing the valve to open.

The effectiveness of supplemental or complete respiration can be determined by observing the blood gas parameters of the patient. Adequate ventilation of the patient is indicated if the blood contains appropriate levels of oxygen and carbon dioxide. However, it has not been feasible to monitor blood gases continuously.

Although periodic blood gas measurements can still be taken, a more immediate indication of loss of ventilation is needed, as ventilation loss for more than one minute can be fatal. Consequently, most ventilator monitors measure the volume of gas used to ventilate the patient. The measured gas volume has been either the volume of gas supplied to the patient or the volume of gas expired by the patient. Expiratory monitoring avoids the adverse effects of loss of patient ventilation through leaks in the gas flow system. Leaks may cause some of the expired gas volume to escape detection by the monitor; however, the operator is assured that the patient receives at least as much of the ventilator output as is detected. On the other hand, if the output of the ventilator is monitored before the gas reaches the patient, there is no positive indication as to the minimum gas volume that reaches the patient since this gas flow system may have inherent leaks between the monitor and the patient.

Expiratory gas volume is measured by connecting the monitor to the output port of the expiration valve. The expiration valve ideally will permit the free-flow of expired gas from the patient to the monitor, and block the flow to the monitor of the inspiratory gas from the ventilator to the patient. There are many reasons why the expiration valve may leak, e.g. a defective diaphragm, a defective valve seat, a leak in the pneumatic valve control line so that the valve diaphragm is not fully closed, or a build-up of patient secretions in the valve. Secretions from the patient build-up between the expiration valve diaphragm and the valve seat causing gas leakage during inspiration. These secretions prevent complete closure of the expiration valve since the pressure applied to inflate the expiration valve diaphragm is typically only 1.5 to 3.0 PSI. This range of pressures is not sufficient to break through the secretions to achieve closure of the valve pipe against a back pressure that is nearly equal to the diaphragm control pressure. When leakage occurs, the volume of gas measured by the monitor will contain gas expired by the patient and that which leaked through the valve during inspiration. Therefore, the measured gas volume will be greater than that expired by the patient. In the extreme case where the valve leaks continuously in a fully open condition, the volume of gas measured by the monitor indicates that normal gas volume is being delivered to the patient, when in fact the patient has received none of the measured gas volume. Heretofore known monitors had no mechanism for distinguishing when the received gas was from the patient or from the ventilator. These monitors relied on the possibly leaky expiration valve to block the inspiratory gas from the ventilator.

Since the expiration valve must be sterilized, and the pneumatically controlled valves must be operational from the ventilator low pressure control line, only limited improvements are possible in the expiration valve itself. Many hospitals prefer to use disposible items wherever possible, thus placing a cost limitation on the expiration valve, in addition to the aforementioned limitations. The failure of the expiration valve is not readily detectable with the present monitors. Thus, a blood gas analysis is the method relied upon by the doctor and his staff to insure the proper ventilation of the patient.

Summary of the Invention

The present invention provides a fail-safe feature in the ventilator monitor circuitry to insure accurate measurement of expired gas volume from a patient despite the use of a leaky expiration valve. The system of the present invention is compatible with IPPB ventilators presently commercially available. An accurate patient expiration signal is generated by a ventilator patient monitor to electrically block the inclusion of a volume of gas leaked through a partially closed expiration valve from a volume of gas expired by the patient. There are derived signals representing expiratory flow rate and the volume of the gas expired by the patient. The accurate expiration signal gates the flow rate signal in such a way as to eliminate the adverse effects of a leaky expiration valve. The gated flow rate signal is then integrated over time to obtain the volume of gas expired by the patient. Thus, the gas volume recorded by the monitor is substantially equal to the expired gas volume of the patient.

In the illustrated embodiment of the invention, the accurate expiration signal which controls volume monitoring is generated by processing both a detected flow rate through the expiration valve and a detected mouth or air-way pressure of the patient. The method of generating the accurate expiration signal is independent of the type of expiration valve control signal from the ventilator, and thus can be used with any IPPB ventilator. Expiration is defined as that period of time when the expiration valve flow resistance is below a preselected threshold resistance. The gas flow through the expiration valve is monitored and processed to provide four signals: a first-estimate expiration signal; a gas flow-rate signal; an expired gas volume signal; and an expiration rate signal. Simultaneously, the mouth or air-way pressure of the patient is monitored and processed to provide three signals: a real-time mouth pressure signal; a maximum mouth pressure signal; and a minimum mouth pressure signal. The first two signals derived from the gas flow, and the first signal obtained from the mouth or air-way pressure are further processed and used to compare an estimate of the real-time resistance value of the expiration valve with the preselected threshold resistance value. When the valve resistance is less than the preselected threshold value, the expiration valve is defined to be open. This defined open time is indicated by the accurate expiration signal, which in turn controls the integration of the gas flowrate signal to provide an accurate representation of gas volume expired by the patient, independent of the valve leaks.

Description of the Drawings

FIGS. 3(a) and (b) are waveforms illustrating the sequence of operation of some of the system components in the illustrated embodiment.

Description of the Preferred Embodiment

Figure 1:
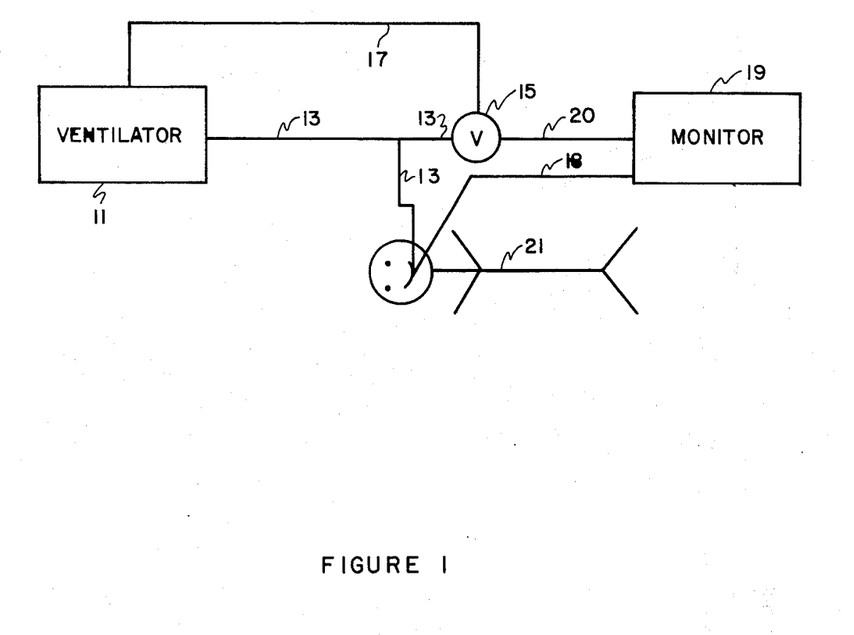
FIG. 1 is a block diagram illustrating the ventilator patient monitor interconnections.

With reference to FIG. 1, there is shown an IPPB ventilator 11, tubing 13 for directing the gas flow, an expiration valve 15, an expiration valve control line 17, a mouth or air-way (i.e. any air passage, natural or created, to provide patient ventilation) pressure detection line 18, a ventilator patient monitor 19, a monitor gas flow input tube 20, and a patient 21. During an inspiration cycle, the expiration valve control line 17 is activated by the ventilator 11 to maintain closure of the expiration valve 15. Then the gas is pumped from ventilator 11, to patient 21, through tubing 13. Next, the gas flow from the ventilator 11 ceases, the expiration valve control line 17 is deactivated, thus allowing the opening of the expiration valve 15, and patient 21 expires, i.e., exhales the gas in his lungs without assistance. The expired gas flows to monitor 19 through tube 20. The monitor measures the gas volume and displays the measured value. An error in the measurement of the expired gas volume from patient 21 occurs if the expiration valve 15 is not fully closed during inspiration and leaks result. Heretofore known monitors do not eliminate the effect of the volume of leaked gas from the expired gas volume measurement.

Figure 2:
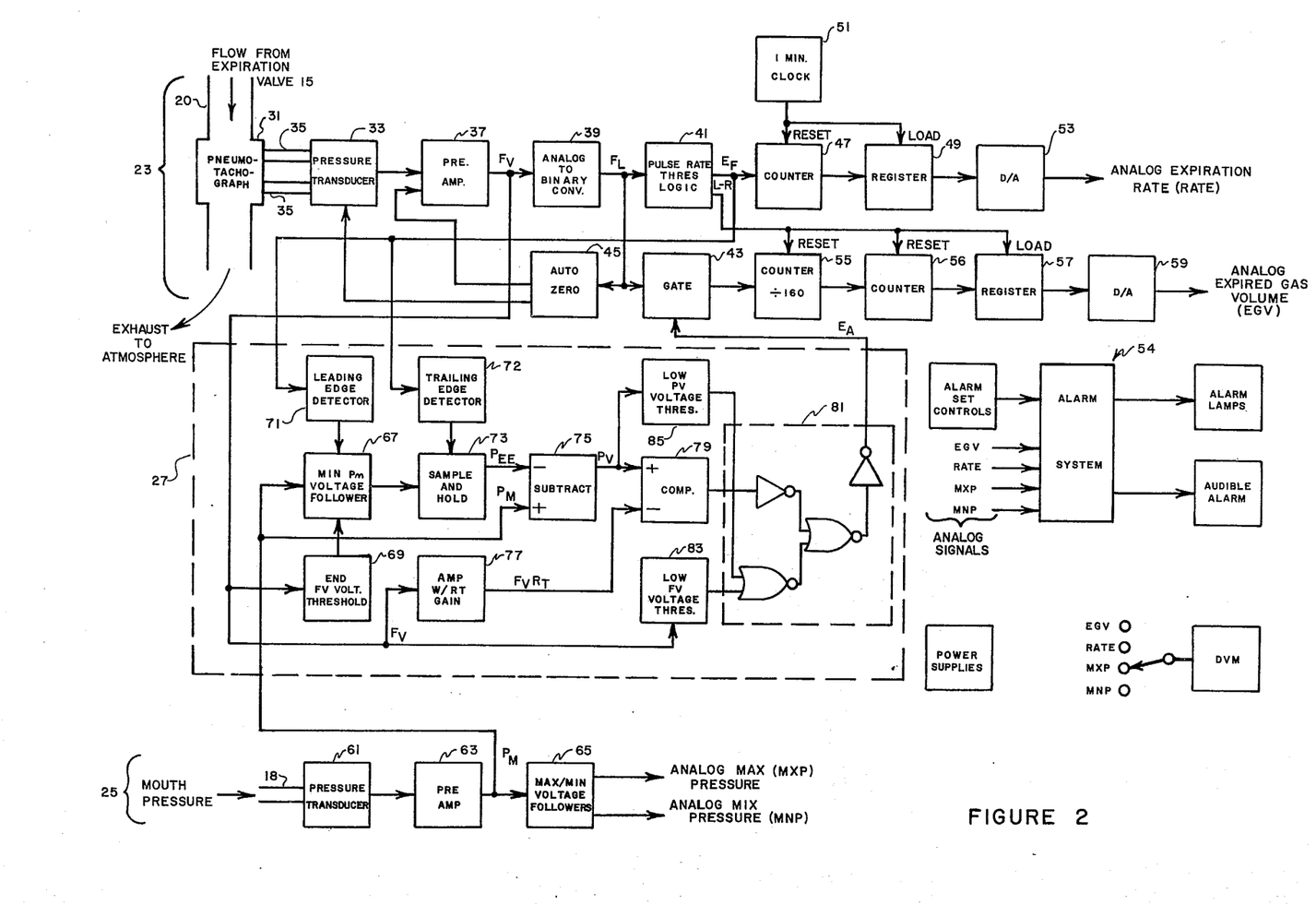
FIG. 2 is a block diagram illustrating the preferred embodiment of the system of the present invention.

The preferred embodiment of the invention illustrated in FIG. 2 comprises a gas flow processing channel 23 to provide expiration rate and expired gas volume signals, a mouth or airway pressure processing channel 25 to provide maximum and minimum mouth or air-way pressure signals, and an accurate expiration signal generating circuit 27 to provide a gating signal to eliminate the adverse effects of a leaky expiration valve from the expired gas volume signal.

In gas flow channel 23 the input element is a pneumotachograph 31 coupled to the output port of the expiration valve 15 by tube 20 (FIG. 1). The pneumotachograph 31 includes a resistance element which provides a pressure differential across a pair of output ports that is proportional to the gas flow rate. The output ports of the pneumotachograph 31 are coupled to a differential input pressure transducer 33 by means of tubing 35. The pressure differential developed by the gas flow across the output ports of pneumotachograph 31 is typically on the order of 0.015 PSI when the flow rate is three liters per second. Transducer 33 is a very low pressure transducer that provides an output current proportional to the flow rate, and this current is applied to preamplifier 37 for conversion to a voltage signal and linearization. Linearization is necessary because at higher patient expiratory flow rates the pneumotachograph 31 becomes nonlinear. The linearized signal from the preamplifier 37 is an analog representation of the gas flow-rate $F_v$, through the expiration valve 15 (FIG. 1). The output of circuitry 37 is applied to an analog-to-binary converter 39 which may be of the type described in U.S. Pat. No. 3,659,288 issued Apr. 25, 1972, and now assigned to the same assignee as the present invention. The output of circuit 39 is a continuously variable frequency square wave signal that is a logical gas flow-rate signal, $F_L$, typically as shown by signal 40 in FIG. 3a. More particularly, each pulse represents a gas volume of 1/16000 of a liter per pulse, and the flow-rate information is represented by the frequency of this square wave signal, this frequency increasing linearly with an increasing linear analog input voltage from preamplifier 37.

The output signal of circuit 39, $F_L$, is applied to three circuits: a pulse rate threshold logic circuit 41, a gating circuit 43, and an automatic zero circuit 45. Since the output signal of transducer 33 drifts with time, the automatic zero circuit 45 periodically determines this signal drift and applies a feedback signal to a second input of preamplifier 37 that is proportional to the signal drift. This feedback signal to preamplifier 37 is then subtracted from the output signal of transducer 33, so that the output of preamplifier 37 does not reflect the drift-caused offset of transducer 33. The determination of the necessary correction signal for preamplifier 37 is accomplished by disconnecting transducer 33 from pneumotachograph 31 so that the differential pressure input to transducer 33 is zero. Thereafter sufficient time is provided for the automatic zero circuit to detect the steady-state output frequency of circuit 39, and to generate and hold a signal level proportional to this frequency that is applied to preamplifier 37. Thus, the output of the analog-to-binary converter 39 is corrected such that a zero frequency output corresponds to a zero gas flow rate.

Figure 3:
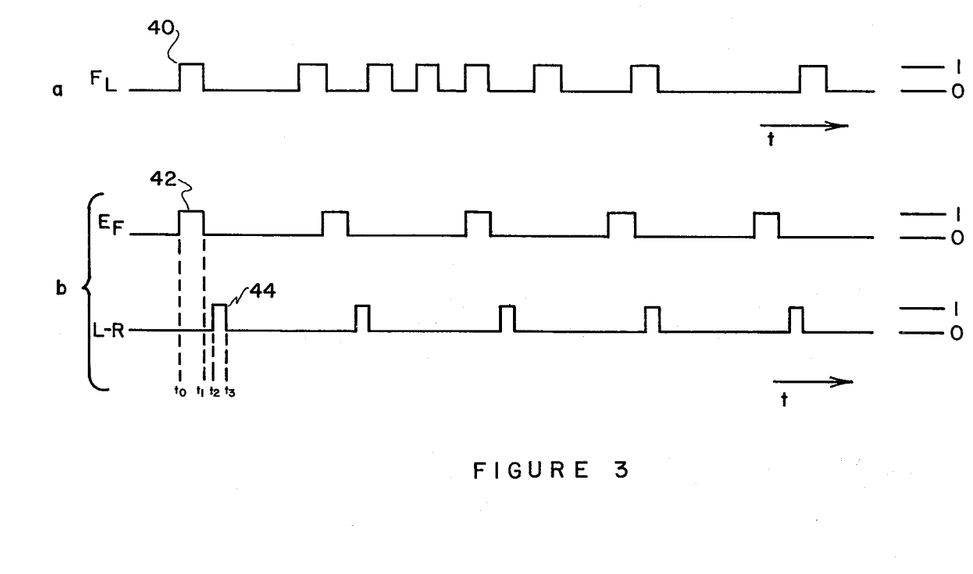

With reference to FIG. 3b, the pulse rate threshold logic circuit 41 generates two output signals. One of these is a first-estimate expiration signal, $E_F$, shown as pulse train 42. The other output signal is a load-reset signal, L-R, as shown by pulse train 44 (FIG. 3b), and is hereinafter described. Circuit 41 includes two pulse-rate threshold circuits. One is an increasing pulse-rate threshold detector, and the second is a decreasing pulse-rate threshold detector. The outputs of circuit 41 remain a logical 0 until the pulse rate of signal 40 exceeds a preset threshold pulse rate for a preset period of time, then the first-estimate expiration signal 42 will attain a logical 1 at time $t_o$ and will retain that level until the pulse rate drops below a second preset threshold level for a second preset period of time. After the second threshold is crossed and the second preset time period expires, the first-estimate expiration signal 42 will reassume the logical 0 level at time $t_1$. The result is that the first-estimate expiration signal 42 becomes a logical 1 shortly after expiration starts and returns to a logical 0 toward the end of expiration. The first-estimate expiration pulses from the pulse rate threshold logic circuit 41 are then counted by counter 47 for a period of one minute determined by a clock 51. At the end of one minute, the count in counter 47 is loaded into a digital register 49 by clock 51. Counter 47 is then reset by clock 51 and immediately starts counting the number of first-estimate expiration pulses 42 for the next one minute period. The count, which is held in register 49, is then applied to a digital-to-analog converter 53 for conversion to an analog voltage that is proportional to the number of breaths that patient 21 has taken during the next previous one minute interval. The analog expiration rate voltage from converter 53 is then applied to a RATE input of an alarm system 54. The alarm system 54 provides an upper and a lower threshold level for each of the input signals. Thus, if the expiration rate voltage is greater than or less than these preset upper and lower alarm threshold levels respectively, the audible and visible alarms are initiated.

Since each pulse of the logical gas flow-rate signal 40 from circuit 39 represents a volume of 1/16000 of a liter, this signal can be integrated by counting the pulses to provide a signal representative of gas volume. A series coupled pair of counters 55 and 56 receives these pulses from gate circuit 43 and counts them to determine the gas volume of the patient expired flow. Gate circuit 43 transmits the pulses in response to a control signal described hereinafter. Counter circuit 55 divides the output pulses from gate 43 by 160, and counter 56 accumulates the gas volume count in units of 0.01 liters from counter 55. Circuit 41 produces a second signal pulse train 44, i.e., the load-reset pulse train (FIG. 3b), that becomes a logical 1 shortly after each first-estimate expiration pulse 42 reassumes the logical 0 level. Pulse 44 remains a logical 1 for a preset length of time after which it returns to a logical 0. The leading edge of load-reset pulse 44 loads the count from counter 56 into a digital register 57 by actuating the load input line of register 57. The trailing edge of pulse 44 then resets counters 55 and 56 to zero by actuating the reset lines of counters 55 and 56 in preparation for measuring the gas volume count on the next expiration of the patient. The expired gas volume value that is stored digitally in the register 57 is applied to the digital-to-analog converter 59 to provide an analog expired gas volume signal which in turn is applied to the EGV input of alarm system 54. The alarm system 54 also provides upper and lower threshold limits for the expired gas volume signal, and a visual and audible alarm is initiated if either threshold is crossed.

In mouth pressure channel 25, the mouth or air-way pressure of patient 21 is transmitted to a pressure transducer 61 by tube 18. Tranducer 61 then converts the mouth pressure, typically in the range of ±1.5 PSI, to an electrical signal which is proportional to the mouth pressure. This signal is then applied to preamplifier 63 to provide voltage scaling of the output signal of pressure transducer 61. The output signal of preamplifier 63 is then an analog mouth pressure signal, $P_M$, which is linearly related to the actual mouth pressure of the patient 21. This analog mouth pressure signal is then applied to a maximum-minimum voltage follower circuit 65. Voltage follower circuit 65 comprises two pairs of voltage followers, one pair of increasing voltage followers for tracking and holding the maximum input voltage over a preset time period, and a second pair of decreasing voltage followers for tracking and holding the minimum input voltage over the same preset time period. Each pair of voltage followers are essentially the same, and each voltage follower includes two operational amplifiers whose outputs are connected through diodes to a capacitor. One of these two operational amplifiers in each of the voltage followers is used to charge or discharge the capacitor if the circuit is a maximum or a minimum voltage follower respectively. The second voltage follower operational amplifier is used to reset the capacitor voltage to preset values below the lowest expected maximum voltage, or above the highest expected minimum voltage. The voltage followers for both the maximum and the minimum voltage are paired so that a continuous indication of the tracked voltage is always available from one of the voltage followers while the other is reset to provide an updated value. The voltage followers are reset alternately at a preset rate with one of each of the maximum and the minimum followers being reset simultaneously. A switching arrangement is utilized on the output of each follower pair to provide a measure of the maximum and minimum mouth pressure stored during the last previous measurement period. The resulting maximum and minimum voltages are representative of the maximum and minimum mouth pressures of the patient. The alarm system 54 is provided with these signals representative of the maximum and minimum mouth or air-way pressure of the patient on alarm input lines MXP and MNP respectively. The alarm system 54 includes an upper and lower voltage threshold for each of these signals, and an alarm indication will be initiated if these signal thresholds are crossed.

The circuit for generating the accurate expiration signal enclosed in dashed outline 27 relies on a method by which the resistance of expiration valve 15 is compared with a selected threshold resistance value to determine if valve 15 is open or closed. Basically, valve resistance will be higher during patient inspiration than during patient expiration. By setting an appropriate threshold, inspiration is defined as the time when the valve resistance is above the threshold resistance, and expiration is defined as the time when the valve resistance is below the threshold resistance. Valve resistance can be defined as:

$$R_V = P_V/F_V \qquad (1)$$

where $R_V$ is the valve resistance, $P_V$ is the pressure across the valve, and $F_V$ is the flow through the valve. This formula can be rewritten as:

$$F_V R_V = P_V. \tag{2}$$

Substituting the preselected valve threshold resistance, $R_T$, for the valve resistance, $R_V$, in equation (2), an inequality results. If the comparison of the product $F_V R_T$ with $P_V$ results in the following inequality $$F_V R_T \leq P_V, \tag{3}$$

then $$R_V \geq R_T \tag{4}$$

and inspiration of the patient is assumed. Otherwise, if the same comparison results in the following inequality $$F_V R_T > P_V, \tag{5}$$

then $$R_V < R_T \tag{6}$$

and expiration of the patient is assumed.

An accurate expiration signal, $E_A$, that is representative of the relationship between $R_T$ and $R_V$ (i.e., representative of the inspiration or expiration of the patient) is the output of the circuit within broken outline 27, and is the result of a comparison that results in equations 3 and 5 above. To generate $E_A$, the circuit within broken outline 27 requires two signals from the flow channel 23 and one signal from the mouth pressure channel 25. The two signals from the flow channel 23 are the first-estimate expiration signal 42, $E_F$, and the analog gas flow-rate signal, $F_V$, from preamplifier 37. The required signal from channel 25 is the analog mouth pressure signal, $P_M$. The signal $P_M$ is used to generate an estimate of $P_V$, i.e. the pressure across expiration valve 15. The difference between the mouth pressure, $P_M$, at any given time and the mouth pressure at the end of an expiratory cycle, $P_{EE}$, is a good estimate of the pressure, $P_V$, across expiration valve 15. The mouth pressure when the flow rate falls to zero or some very small value is a good approximation of the time when the end of expiratory pressure, $P_{EE}$, exists within the mouth of patient 21. To generate $P_V$, the first-estimate expiration signal, $E_F$, is applied to differentiator inputs of a pair of edge detectors 71 and 72. The analog mouth pressure signal, $P_M$, is applied to a minimum $P_M$ voltage follower circuit 67 and a substract circuit 75. The analog gas flow-rate signal, $F_V$, is applied to an end $F_V$ voltage threshold circuit 69.

The purpose of circuits 67, 69, 71, 72 and 73 is to obtain an estimate of $P_{EE}$ within the mouth of the patient. Initially, the output voltage of a minimum $P_M$ voltage follower circuit 67 has been set by circuit 71 to be above the voltage which represents the maximum expected mouth pressure. After circuit 67 has been reset by $E_F$, via circuit 71, and before $E_F$ returns to a logical 0 level, $F_V$ from circuit 37 should exceed the preset threshold level of an end $F_V$ voltage threshold circuit 69. When $F_V$ exceeds this threshold, voltage follower 67 is enabled by the output of circuit 69 to follow the voltage $P_M$. Circuit 67 will follow the voltage $P_M$ to some minimum value during the time period established by $E_F$ maintaining a logical 1 level and $F_V$ exceeding the preset threshold level of circuit 69. When $F_V$ crosses this threshold, the decrease of the output voltage of the minimum $P_M$ voltage follower circuit 67 is stopped. When the first-estimate expiration pulse $E_F$ becomes a logical 0 at the end of expiration, the trailing edge detector circuit 72 enables a sample and hold circuit 73 to receive the output voltage of the minimum $P_M$ voltage follower 67. The retained voltage of the sample and hold circuit 73 represents the estimate of $P_{EE}$ within the mouth of the patient. When the first-estimate expiration signal, $E_F$ goes high during the next expiration of the patient, the leading edge detector circuit 71 triggers the minimum $P_M$ voltage follower circuit 67 to reset the output voltage to a level that represents a pressure greater than an expected mouth pressure, and the process begins again. The voltage follower circuit 67 is very similar to one half of the minimum voltage follower portion of circuit 65. The estimated $P_{EE}$ voltage at the output of circuit 73 is then subtracted from the mouth pressure signal, $P_M$, at the output of circuit 63 on a real-time basis by subtract circuit 75. The resulting output voltage from circuit 75 is an estimate proportional to the real-time valve pressure, $P_V$.

Amplifier 77 receives the analog gas flow-rate signal, $F_V$, from circuit 37 and has a gain equal to the preselected threshold resistance, $R_T$, of the expiration valve 15 (FIG. 1). Thus, the output of circuit 77 represents the product of the valve flow, $F_V$, and the valve threshold resistance, $R_T$. A comparator 79 with a digital output is used to compare the valve pressure signal, $P_V$, on the positive input terminal and the signal that represents the product of valve flow rate, $F_V$, and threshold resistance, $R_T$, on the negative input terminal. If the output voltage of comparator 79 is a logical 1, then the actual valve resistance is greater than the valve threshold resistance, and if the output voltage of the comparator 79 is a logical 0, the actual vale resistance is less than the valve threshold resistance. Thus, a comparator output voltage that is a logical 1 indicates that the expiration valve 15 is closed, and an output voltage that is a logical 0 indicates that the expiration valve 15 is open.

In some cases, there may be excessive noise on the analog flow-rate signal, $F_V$, and the valve pressure signal, $P_V$. With noise present, the output signal from comparator 79 may be unstable when the valve pressure signal, $P_V$, and the product signal, $F_V R_T$, are substantiallly equal. To overcome this instability two valve threshold resistance values, $R_{T1}$ and $R_{T2}$, are used. By using two valve resistance thresholds, an hysteresis effect can be utilized to cause the state of the valve condition indicating signal (i.e. input to inverter of gating circuit 81 in FIG. 2) to change only after both thresholds are crossed. $R_{T1}$ is selected to be the minimum and $R_{T2}$ is selected to be the maximum expiration valve resistance threshold values that define an open versus a closed expiration valve.

Figure 4:
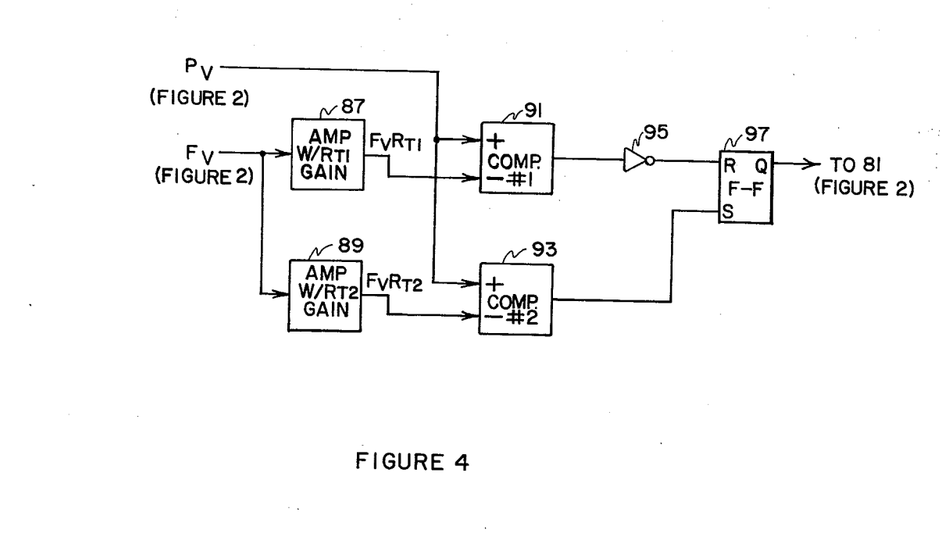
FIG. 4 is a block diagram illustrating another embodiment of a portion of the instant invention.

The alternative embodiment of FIG. 4 can be used to directly replace amplifier 77 and comparator 79 in FIG. 2 to provide the above-described hysteresis effect. Amplifiers 87 and 89 each receive the analog gas flow-rate signal, $F_V$, from circuit 37 (FIG. 2) and each has a gain equal to one of the two preselected threshold resistances, $R_{T1}$ and $R_{T2}$ respectively, of the expiration valve 15 (FIG. 1). Thus, the outputs of circuits 87 and 89 represent the product of the valve flow, $F_V$, and the respective valve threshold resistance, $R_{T1}$ or $R_{T2}$. A pair of comparators 91 and 93 each with a digital output are used to compare the valve pressure signal, $P_V$, on the positive input terminals with one of the signals that represent the product of the valve flow rate, $F_V$, and one of the threshold resistances, $R_{T1}$ and $R_{T2}$, on the negative input terminals respectively. If the output voltage of comparator 91 or 93 is a logical 1, then the actual valve resistance is greater than the valve threshold resistance, $R_{T1}$ or $R_{T2}$ respectively, and if the output voltage of comparator 91 or 93 is a logical 0, the actual valve resistance is less than the valve threshold resistance, $R_{T1}$ or $R_{T2}$, respectively. Since $R_{T1}$ is selected to be less than $R_{T2}$, an inverter 95 and an R-S flip-flop 97 will provide the aforementioned hysteresis effect, i.e. the indicated state of the expiration valve will be unchanged until both thresholds are crossed. To implement this hysteresis effect, the comparison signal of the actual valve resistance with the lower valve threshold resistance, $R_{T1}$, from comparator 91 is applied to the R terminal of flip-flop 97 via inverter 95. Also, the second comparison signal of the actual valve resistance with the higher valve threshold resistance, $R_{T2}$, from comparator 93 is applied to the S terminal of flip-flop 97. Thus, the Q output signal of flip-flop 97 is a logical 1 when the expiration valve 15 is closed, and is a logical 0 when the expiration valve 15 is open.

Figure 5:
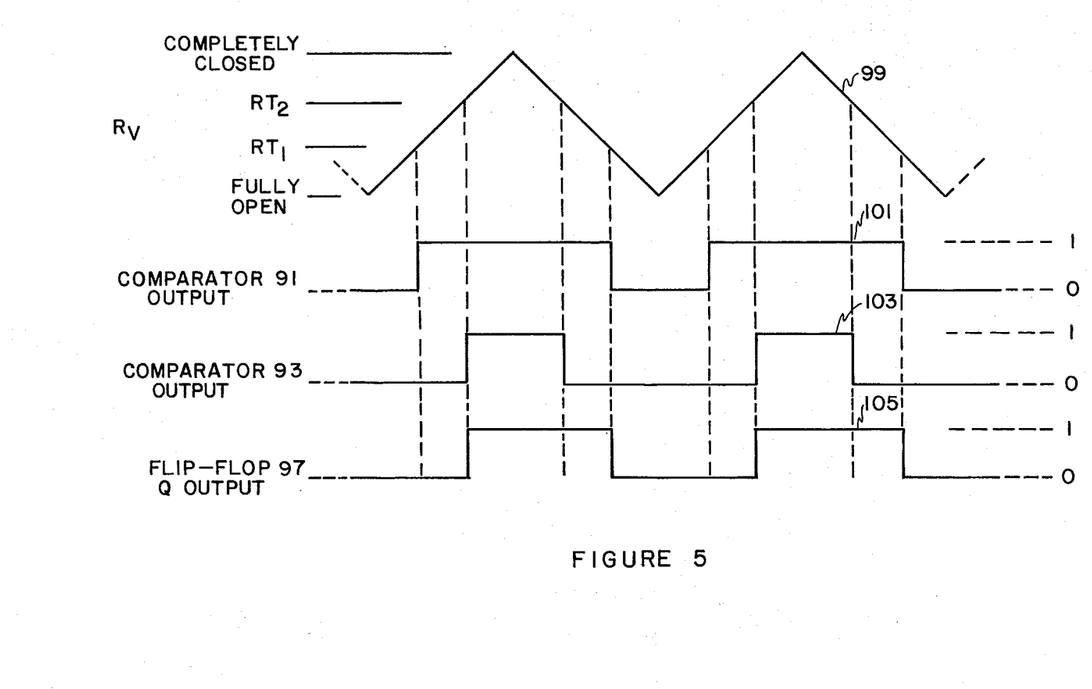
FIG. 5 is a set of waveforms illustrating the sequence of operation of the other embodiment shown in FIG. 4.

FIG. 5 illustrates the hysteresis effect of the circuit in FIG. 4. Assume that the actual valve resistance, $R_V$ varies as depicted by waveform 99. As the actual valve resistance increases from the fully open valve the output of comparator 91 assumes a logical 1 level after the first resistance threshold, $R_{T1}$, is exceeded as shown in waveform 101. As $R_V$ continues to increase, the output of comparator 93 assumes a logical 1 level after the second resistance threshold, $R_{T2}$, is exceeded as shown in waveform 103. Similarly, as $R_V$ decreases the outputs of comparators 93 and 91 assume a logical 0 level after the respective threshold levels, $R_{T2}$ and $R_{T1}$, are crossed. Waveform 105 shows the resultant Q output signal of flip-flop 97 as the outputs of comparators 91 and 93 switch as $R_V$ varies. Waveform 105 assumes a logical 1 level when both waveforms 101 and 103 assume a logical 1 level with an increasing $R_V$, and assumes a logical 0 level when both waveforms 101 and 103 assume a logical 0 level with a decreasing $R_V$. Thus, the Q output signal of flip-flop 97 in a logical 1 state indicates that the expiration valve 15 is closed, and in a logical 0 state indicates that the expiration valve 15 is open.

Since the many operational amplifiers used in the circuits of the illustrated embodiment have an inherent voltage offset, the comparator 79 (FIG. 2) or flip-flop 97 (FIG. 4) outputs do not provide an accurate indication of the state of the expiration valve when both the valve flow and the valve pressure simultaneously become very low. As expiration approaches completion, $P_V$ and $F_V$ may be very low simultaneously, and if this occurs, an assumption is made that the valve is open. To include this possibility within the expiration time defined by the accurate expiration signal, the low $P_V$ voltage threshold circuit 85 and a low $F_V$ voltage threshold circuit 83 are used to determine if these signals drop below predetermined low voltage levels. The output signals from circuits 79, 83, and 85 are applied to a gate circuit enclosed within the broken outline 81. The output of circuit 81 is the accurate expiration signal $E_A$, previously described. If both the expiration valve pressure and flow signals ($P_V$ and $F_V$) are below the thresholds of detector circuits 85, and 83, respectively, the output of the respective circuits will be logical 0. Thus, the output of the gate circuit 81 will be logical 1. As a result, the potential error is prevented and the time representing this final portion of expiration is included in the accurate expiration signal, $E_A$. If at least one of the expiration valve pressure and flow signals is high, the $E_A$ output of gate circuit 81 will follow the reciprocal of the output of comparator circuit 79. The output signal of the gate circuit 81 is the accurate expiration signal, $E_A$, which is applied to the control input of gate 43 and used to gate the output of circuit 39. As described above, the accurate expiration signal, $E_A$, gates the logical flow rate signal in such a way as to eliminate the adverse effects of a leaky expiration valve. The gated flow-rate signal is then integrated by counting over time to obtain an accurate measure of the gas volume expired by the patient.

I claim:

1. A method of accurately measuring the gas volume expired by a patient through an expiration valve of a ventilator-patient system, the method comprising the steps of:
   a. monitoring any flow of gas through said expiration valve during the inspiration and expiration phase received by a ventilation-monitor and generating a gas volume signal indicative of the gas flow received by said ventilator monitor;
   b. developing an accurate expiration signal from the ventilator-patient system that defines the time period when the patient is expiring gas from his lungs; and
   c. gating said gas volume signal to a gas volume accumulation register of said ventilator monitor only during the presence of said accurate expiration signal to eliminate from said gas volume signal the monitored gas flow through a leaking expiration valve during inspiration of the patient.

2. The method according to claim 1 wherein the step of developing said accurate expiration signal comprises:
   a. generating a gas flow-rate signal from the gas flow received by said ventilator monitor;
   b. generating a mouth pressure signal from the gas pressure within the mouth of said patient; and
   c. processing said gas flow-rate signal and said mouth pressure signal to determine the time of exhalation of the patient.

3. A method of comparing an expiration valve resistance with at least one of two preselected threshold resistance values to eliminate the inclusion of a measure of the gas volume that leaks through the expiration valve during patient inspiration from a measure of the gas volume expired by the patient, the method comprising the steps of:
   a. generating a gas flow-rate signal from the gas flow through the expiration valve to the ventilator patient monitor;
   b. multiplying said flow-rate signal by at least one of two preselected values to obtain product signals, said preselected values being representative of an expiration valve resistance threshold value that defines an open versus a closed expiration valve.
   c. generating an expiration valve gas pressure signal representative of the gas pressure across the expiration valve;
   d. comparing said gas pressure signal and said product signals to generate a logical comparison signal having a first predetermined state for a valve resistance value that is less than or equal to at least one of the preselected threshold resistance values, and a second predetermined state for a valve resistance value that exceeds at least one of the preselected threshold resistance values;
e. gating said flow-rate signal under the control of said logical comparison signal to limit the resultant flowrate signal to that from the gas flow expired by the patient; and
f. integrating said gated flow-rate signal to obtain a measure of the volume of the gas expired by the patient during that time defined by the logical comparison signal as patient expiration.

4. The method according to claim 3 wherein the step of generating said expiration valve gas pressure signal includes the steps of:
a. generating a real-time mouth pressure signal from the mouth pressure of the patient;
b. generating an end of patient expiration mouth pressure signal from said real-time mouth pressure signal; and
c. subtracting said end of patient expiration mouth pressure signal obtained at the end of a previous expiration from said real-time mouth pressure signal to form a difference signal representing a real-time estimate of the gas pressure across the expiration valve.

5. The method according to claim 4 wherein the step of generating said end of expiration mouth pressure signal includes the steps of:
a. generating a logical first-estimate expiration pulse train from said gas flow-rate signal that assumes a third predetermined state during a first estimate of the expiration time of the patient, and a fourth predetermined state at all other times;
b. threshold detecting said gas flow-rate signal at a preselected minimum level to produce a threshold signal having a fifth predetermined value when the flow-rate signal is below said minimum level and being representative of the flow-rate signal when said minimum level is exceeded, said preselected minimum level being representative of the gas flow-rate from the patient when expiration starts and ends; and
c. tracking said real-time mouth pressure signal, during the time period when both said first-estimate expiration signal is in the third predetermined state and said gas flow-rate signal exceeds said preselected minimum level, to produce said end of expiration mouth pressure signal.

6. The method according to claim 3, wherein the step of comparing said gas pressure signal and said product signals to generate said logical comparison signal further includes generating an accurate expiration signal to control the gating of said flow-rate signal, the generating of said accurate expiration signal including the steps of:
a. generating a flow-rate threshold signal from said flow-rate signal with said first predetermined state if the flow-rate signal is below a preselected signal level and said second predetermined state when the flow-rate signal exceeds the preselected signal level, said preselected signal level being representative of a minimum gas flow-rate defining expiration;
b. generating an expiration valve pressure threshold signal from said difference signal with said first predetermined state if the difference signal is below a preselected signal level and said second predetermined state when the difference signal exceeds the said preselected signal level, said preselected level being representative of a minimum expiration valve pressure defining expiration; and
c. gating the flow-rate threshold signal, the pressure threshold signal, and said logical comparison signal to generate said accurate expiration signal having said first and second predetermined states, the state of the accurate expiration signal being said second predetermined state when said pressure and flow-rate threshold signals are simultaneously in said first predetermined state, and the reciprocal of said logical comparison signal at all other times to include within the expiration time the time when said flow-rate and said difference signal levels are simultaneously below the preselected threshold levels.

7. A ventilator monitoring system responsive to the mouth pressure of a patient and the gas flow through an expiration valve to measure the gas volume expired by the patient by eliminating the inclusion of the measured volume of the gas flow through a leaking expiration valve during inspiration of the patient from the total measured volume of the monitored gas flow from the expiration valve, said system comprising:
first means coupled to the mouth of the patient for detecting gas pressure within the mouth and generating a mouth pressure signal;
second means coupled to an output port of said expiration valve for measuring the gas flow through said valve and for generating a gas flow-rate signal and a first-estimate expiration signal;
third means responsive to said mouth pressure signal, said gas flow-rate signal, and said first-estimate expiration signal for generating an accurate expiration signal that defines the time period that the patient is expiring gas from his lungs; and
fourth means responsive to said accurate expiration signal for gating said gas flow-rate signal to permit integration of a portion of the flow-rate signal to provide a measure of the patient expired gas volume, said gating being operable to eliminate the inclusion of that portion of the flow-rate signal corresponding to the inspiratory gas leaking through the expiration valve from the gas flow-rate signal that corresponds to the expiratory gas from the patient, thereby to limit the gas volume value obtained by integration to the volume of gas expired by the patient.

8. The ventilator monitoring apparatus as in claim 7 wherein said first means comprises:
a pressure transducer coupled to the mouth of the patient; and
means for amplifying the output of said pressure transducer to provide a mouth pressure signal that varies linearly with the mouth pressure of the patient.

9. The ventilator monitoring apparatus as in claim 7 wherein said second means comprises gas flow-rate detection means coupled to the output port of the expiration valve, said gas flow-rate detection means having an output signal that is linearly related to the gas flow-rate through the expiration valve.

10. The ventilator monitoring apparatus as in claim 7 wherein said third means comprises:
valve pressure estimation means responsive to said analog mouth pressure signal, said analog gas flow-rate signal, and said first estimate expiration signal for generating a signal representative of the pressure across the expiration valve;

valve condition indicating means responsive to said valve pressure estimation means and said gas flow-rate signal for generating a logical signal having a first predetermined state defining an open valve, and a second predetermined state defining a closed valve;

a low valve pressure voltage threshold circuit coupled to the output of the valve pressure estimation means to provide a logical indication of the first predetermined state when the signal representing the valve pressure falls below a preset level, and the second predetermined state when the signal representing the valve pressure exceeds the preset level, said preset level being representative of a valve pressure threshold value that defines a valve pressure error level;

a low valve flow-rate voltage threshold circuit coupled to the gas flow-rate signal to provide a logical indication of the first predetermined state when the signal representing the gas flow-rate falls below a preset level, and the second predetermined state when the gas flow-rate signal exceeds the last-named preset level, said last-named preset level being representative of a gas flow-rate threshold value that defines a gas flow-rate error level; and gating circuit means responsive to inputs from the valve condition indicating means, the low valve pressure voltage threshold circuit, and the low valve flow-rate voltage threshold circuit for generating said accurate expiration signal having said first and second predetermined states, the state of the accurate expiration signal being said second predetermined state when said pressure and flow-rate threshold circuits are simultaneously in said first predetermined state, and the reciprocal of the output of said valve condition indicating means at all other times to include within the expiration time the time when said valve pressure and flow-rate signal levels are simultaneously below the preset threshold levels.

11. The ventilator monitoring apparatus as in claim 10 wherein said valve condition indicating means comprises:

an amplifier circuit coupled to said analog gas flow-rate signal with gain equivalent to a preselected value to obtain an output signal that is proportional to the product of the expiration valve flow-rate and the preselected value, said preselected value being representative of an expiration valve resistance threshold value that defines an open versus a closed expiration valve; and a comparator circuit responsive to the generated expiration valve pressure signal and said valve flow-threshold resistance product signal to provide a logical signal having said first predetermined state if the actual valve resistance is less than said preselected threshold resistance, and said second predetermined state if the actual valve resistance exceeds the preselected threshold resistance.

12. The ventilator monitoring apparatus as in claim 10 wherein said valve condition indicating means comprises:

first amplifier circuit coupled to said analog gas flow-rate signal with gain equivalent to a first preselected value to obtain an output signal that is proportional to the product of the expiration valve flow-rate and the first preselected value, said first preselected value being representative of a minimum expiration valve resistance threshold value that defines an open versus a closed expiration valve;

a second amplifier circuit coupled to said analog gas flow-rate signal with a gain equivalent to a second preselected value to obtain an output signal that is proportional to the product of the expiration valve flow-rate and the second preselected value, said second preselected value being representative of a maximum expiration valve resistance threshold value that defines an open versus a closed expiration valve;

a first comparator circuit responsive to said expiration valve pressure signal and the output signal of said first amplifier circuit to provide a first logical signal having said first predetermined state if the actual valve resistance is less than said first preselected threshold resistance, and said second predetermined state if the actual valve resistance exceeds said first preselected threshold resistance;

a second comparator circuit responsive to said expiration valve pressure signal and the output signal of said second amplifier circuit to provide a second logical signal having said first predetermined state if the actual valve resistance is less than said second preselected threshold resistance, and said second predetermined state if the actual valve resistance exceeds said second preselected threshold resistance;

an inverter circuit responsive to the output of said first comparator circuit; and a flip-flop circuit responsive to the outputs of said inverter circuit and said second comparator circuit to provide an output signal assuming said second predetermined state after the increasing actual valve resistance crosses the second preselected threshold resistance, and the first predetermined state after the decreasing actual valve resistance crosses said first preselected threshold resistance.

13. The ventilator monitoring apparatus as in claim 7 wherein said fourth means comprises:

a gate circuit responsive to said accurate expiration signal and coupled to said scond means to block transmission of that portion of said gas flow-rate signal that is representative of the gas flow that leaks through the expiration valve during patient inspiration; and patient expired gas volume accumulation means coupled to said gate circuit for integrating a gated gas flow-rate signal to provide an expired gas volume signal representative of the volume of gas expired by the patient.

* * * * *

UNITED STATES PATENT AND TRADEMARK OFFICE
CERTIFICATE OF CORRECTION

PATENT NO. : 3,946,729
DATED : March 30, 1976
INVENTOR(S) : Kim L. Hanna

It is certified that error appears in the above-identified patent and that said Letters Patent are hereby corrected as shown below:

Column 8, line 36 "vale" should read -- valve --;

Column 10, line 61 "valve." should read -- valve; --;

Column 14, line 52 "scond" should read -- second --.

Signed and Sealed this

Twenty-fourth Day of August 1976

[SEAL]

Attest:

RUTH C. MASON
*Attesting Officer.*

C. MARSHALL DANN
*Commissioner of Patents and Trademarks*

UNITED STATES PATENT AND TRADEMARK OFFICE
CERTIFICATE OF CORRECTION

PATENT NO. : 3,946,729
DATED : March 30, 1976
INVENTOR(S) : Kim L. Hanna

It is certified that error appears in the above-identified patent and that said Letters Patent are hereby corrected as shown below:

Claim 6, Column 11, line 66, "difference" should read -- gas pressure --; line 67, "difference" should read -- gas pressure --;

Claim 6, Column 12, line 1, "difference" should read -- gas pressure --; line 15, "difference" should read -- valve pressure --;

Claim 11, Column 13, line 57, after "flow-" insert -- rate and preselected valve --.

Signed and Sealed this

Twenty-second Day of March 1977

[SEAL]

Attest:

RUTH C. MASON
*Attesting Officer*

C. MARSHALL DANN
*Commissioner of Patents and Trademarks*